(12) United States Patent
Farley

(10) Patent No.: US 8,753,272 B2
(45) Date of Patent: Jun. 17, 2014

(54) LOW PROFILE SURGICAL RETRACTOR

(75) Inventor: Daniel K. Farley, Traverse City, MI (US)

(73) Assignee: Thompson Surgical Instruments, Inc.

( * ) Notice: Subject to any disclaimer, the term of this patent is extended or adjusted under 35 U.S.C. 154(b) by 578 days.

(21) Appl. No.: 12/357,024

(22) Filed: Jan. 21, 2009

(65) Prior Publication Data

US 2010/0185060 A1    Jul. 22, 2010

(51) Int. Cl.
*A61B 1/32* (2006.01)

(52) U.S. Cl.
USPC ............................... 600/228; 600/232

(58) Field of Classification Search
USPC .................................. 600/201–246
See application file for complete search history.

(56) References Cited

U.S. PATENT DOCUMENTS

| | | | |
|---|---|---|---|
| 4,726,356 A | 2/1988 | Santilli et al. | |
| 4,949,707 A | 8/1990 | LeVahn | |
| 5,167,223 A | 12/1992 | Koros et al. | |
| 6,099,468 A | 8/2000 | Santilli et al. | |
| 6,458,079 B1 * | 10/2002 | Cohn et al. | 600/213 |
| 7,241,264 B2 | 7/2007 | Xiao | |
| 2004/0193018 A1 * | 9/2004 | Thalgott et al. | 600/227 |
| 2004/0242969 A1 * | 12/2004 | Sherts et al. | 600/231 |
| 2005/0038324 A1 * | 2/2005 | Schollhorn | 600/210 |

OTHER PUBLICATIONS

International Search Report and Written Opinion of the International Search Authority, dated Mar. 19, 2010.
Patent Cooperation Treaty, International Preliminary Report on Patentability, in Application No. PCT/US2010/021464, dated Jul. 26, 2011 (6 pages).

* cited by examiner

*Primary Examiner* — Heidi M Eide
(74) *Attorney, Agent, or Firm* — McAndrews, Held & Malloy, Ltd.

(57) ABSTRACT

A retractor clamp is provided for a low profile retractor system including a spreader including first and second arms joined by a cross-bar. The first and second arms define an arm level. The refractor clamp includes a gripping assembly, a main body, an extension arm, a retractor blade arm, and a securement assembly. The refractor clamp is movably and securably joined along the at least one of the first arm, second arm, and cross-bar at substantially the arm level. The refractor blade arm is joined to the main body by the extension arm, and is positioned at a refractor blade arm level above the arm level. The refractor blade arm accepts a blade clamp. The securement assembly includes an adjustment member accessible by an operator substantially at the arm level. The securement assembly is operatively connected to the gripping assembly.

13 Claims, 4 Drawing Sheets

LOW PROFILE SURGICAL RETRACTOR

CROSS-REFERENCE TO RELATED APPLICATION

None.

STATEMENT REGARDING FEDERALLY SPONSORED RESEARCH OR DEVELOPMENT

None.

BACKGROUND OF THE INVENTION

The present invention relates to surgical apparatus for retracting anatomy to provide exposure of an operative site, and more particularly relates to a retraction apparatus providing a low profile.

In surgical operations, retraction devices are used to properly access internal organs and bone structures. Retraction devices are generally designed to hold back the anatomy in the immediate area of the operative site to enable a surgeon to have both an optimal view of the site and a sufficiently-open area within which to work. During a surgical procedure, a surgeon will typically make an incision in a patient to access the sites of interest, such as an internal organ or organs, and/or bone structures, depending on the procedure. A retraction device may then be used to maintain clear access to the site of interest.

For example, during heart surgery, the chest may be opened with an incision along the axis of the sternum. A device may then be used to spread the opening to allow access to the heart. After the sternum is spread, muscular layers of the heart must also be retracted to allow access to the inner portions of the heart which may be required, for example, to replace a mitral valve of the heart. Such procedures may also require a substantial amount of sutures, for example, to sew a valve into the heart. Known retractors currently used for open heart procedures can provide a fairly high profile, and can result in difficulties with accessing the site of interest. For example, sutures may become entangled during such procedures, which can prolong surgery, as well as cause frustration for surgeons. In addition to providing good exposure, reduction of such difficulties and/or causes of frustration are also important factors in successful surgery.

It is therefore one object of the present invention to provide a surgical retractor that provides a retractor with a lower profile, and/or improved access, and/or visibility, and/or improved ease of use around a surgical site of interest.

BRIEF SUMMARY OF THE INVENTION

Certain embodiments of the present invention provide a low profile retractor clamp system, and/or a retractor clamp for a low profile retractor clamp system.

Certain embodiments provide a retractor clamp for a low profile retractor system. The retractor clamp includes a gripping assembly, a main body, an extension arm, a retractor blade arm, and a securement assembly. The gripping assembly is sized and adapted to engage at least one of the first arm, second arm, and cross-bar of a spreader, wherein the retractor clamp is movably and securably joined along the at least one of a first arm, second arm, and cross-bar at substantially an arm level defined by the first and second arms of the spreader. The retractor blade arm is joined to the main body by the extension arm, and is positioned at a retractor blade arm level above the arm level. The retractor blade arm is sized and adapted to accept a blade clamp for securing a retractor blade thereto. The securement assembly includes an adjustment member sized and adapted to be accessible by an operator at an elevation substantially at the arm level. The securement assembly is operatively connected to the gripping assembly.

In certain embodiments, the retractor blade arm may be substantially perpendicular to the extension arm, and extend from the extension arm in a single direction, forming an "L" shape. Further, the extension arm may extend from the main body at an obtuse angle. For example, the main body may include a top surface, and the extension arm may extend from the main body at about 120 degrees from the top surface. In certain embodiments, the retractor blade arm extends generally parallel to the at least one of the first arm, second arm, and cross-bar when the retractor clamp is secured in place.

In certain embodiments, the securement assembly includes a threaded member extending substantially at the arm level and substantially perpendicular to the at least one of the first arm, second arm, and cross-bar when the retractor clamp is secured to the at least one of the first arm, second arm, and cross-bar. The adjustment member includes a knob joined to an end of the threaded member. Additionally, the gripping assembly may include a clamp slide engaged by the threading member, wherein the clamp slide is actuated by the rotation of the knob.

Certain embodiments provide a low profile retractor system including a spreader, a retractor clamp, a retractor blade, and a retractor blade clamp. The spreader includes first and second arms joined by a cross-bar. The first and second arms are generally parallel and define an arm level. The retractor clamp is movably and securably joined along at least one of the first arm, second arm, and cross-bar at substantially the arm level. The retractor clamp includes a main body, an extension arm, a retractor blade arm, and a securement assembly. The extension arm extends proximal from the main body to the retractor blade arm. The retractor blade arm is at a retractor blade arm level above the arm level, and extends at the retractor blade arm level in a direction generally parallel to the at least one of the first arm, second arm, and cross-bar to which the retractor clamp is secured. The retractor blade arm is sized and adapted to accept a clamp for securing a retractor blade there to. The securement assembly engages the main body and includes an adjustment member sized and adapted to be accessible by an operator at an elevation substantially at the arm level. The retractor blade include a handle and a blade, the retractor blade clamp is sized and adapted to accept the retractor blade arm and the handle of the retractor blade.

In certain embodiments, the low profile retractor system includes a first retractor blade having a first handle and a first blade, and a second retractor blade having a second retractor and a second blade. The first handle and second handle may be different lengths. Further, the first and second blades may be substantially the same size and shape.

DETAILED DESCRIPTION

Figure 1:
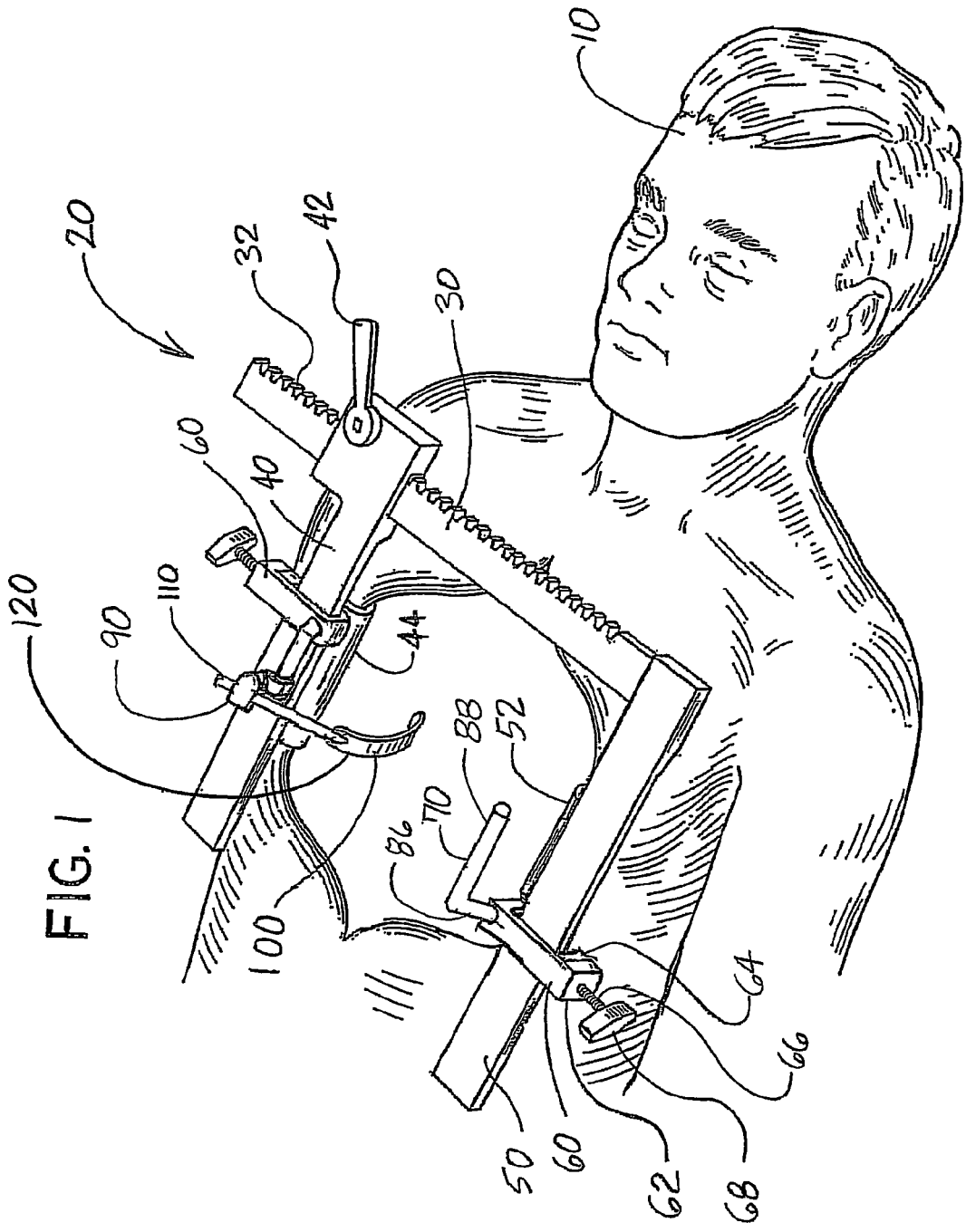
FIG. 1 presents an isometric view of a low profile retractor system formed in accordance with an embodiment of the present invention being used to assist in obtaining access to a chest cavity of a patient.

FIG. 1 presents an isometric view of a low profile retractor system 20 being used to assist in obtaining access to a chest cavity of a patient 10 during, for example, an open heart procedure. The low profile retractor system 20 includes a cross-bar 30, a first arm 40, and a second arm 50. The low profile retractor system 20 also includes a retractor clamp 60, a blade clamp 90, and a retractor blade 100. The low profile retractor system 20 may include components made of stainless steel, for example.

In the illustrated embodiment, the cross-bar 30 is joined substantially perpendicularly to the first arm 40 and second arm 50, with the first arm 40 and second arm 50 substantially parallel to one another. The cross-bar 30, first arm 40, and second arm 50 may be joined, for example, to form a sternum spreader. Further, the cross-bar 30 includes teeth 32, which form a rack extending along at least a portion of the length of cross-bar 30. The teeth 32 interact with a gear located in the first arm 40 (not shown) as a rack and pinion. The first arm 40 includes a crank 42 which may be turned to actuate the gear to position the first arm 40 along the length of the cross-bar 32. When the first arm 40 is positioned as desired, the position of the first arm 40 may be locked in. In the illustrated embodiment, the second arm 50 is fixed in relation to the cross-bar 30. Thus, by turning the crank 42 and adjusting the position of the first arm 40 along the length of the cross-bar, the distance between the first arm 40 and the second arm 50 may be increased or decreased.

The first arm 40 includes a retracting portion 44, and the second arm 50 includes a retracting portion 52. In the illustrated embodiment, each of the retracting portions 44, 52 extend from a bottom surface of the first arm 40 and second arm 50, respectively. Each of the retracting portions 44, 52 are sized and adapted to engage tissue of a patient to retract the engaged tissue away from a surgical site to provide access to the surgical site. For example, in use, a surgeon may first make an incision in the chest cavity of a patient, and the low profile retractor system 20 may be inserted into the resulting opening, with the first arm 40 and second arm 50 relatively close to each other, with the retracting portions 44, 52 engaging the desired tissue of the patient 10. Then, the crank 42 may be turned to increase the distance between the first arm 40 and second arm 50. As the distance is increased, the retracting portions 44, 52 retract the engaged tissue, providing access to the surgical site of interest. Once the desired access has been provided, and the first arm 40 and the second arm 50 are positioned as desired, the position of the first arm 40 along the length of the teeth 32 of the cross-bar 30 may be locked in, securing the system in place.

Additional tissue may be retracted with the use of one or more retractor blades 100. For example, the retracting portions 44, 52 of the first arm 40 and second arm 50, respectively, may be used to retract tissue to proved access inside the chest of a patient. Additional blades 100 may then be used to retract tissue of an organ that is accessed through the previously discussed incision, for example, the heart. As one example, a number of retractor blades 100 may be used to retract tissue of the heart to provide access for a valve replacement. As illustrated in FIG. 1, the low profile retractor system 20 includes a retractor clamp 60, a blade clamp 90, and a retractor blade 100. The retractor clamp 60 is sized and adapted to be securable to and movable along the length of the first arm 40, and/or the second arm 50, and/or the cross-bar 30. The blade clamp 90 is used to secure the retractor blade 100 to the retractor clamp 60. In FIG. 1, to help illustrate various aspects of the low profile retractor system 20, one retractor clamp 60 is illustrated with a retractor blade 100 secured to it with a blade clamp 90, and one retractor clamp 60 is illustrated without a retractor blade 100 or blade clamp 90. In practice, numerous combinations or arrangements of multiple retractor blades 100 could be used, with the retractor blades 100 secured to the first arm 40, and/or second arm 50, and/or cross-bar 30.

Figure 2:
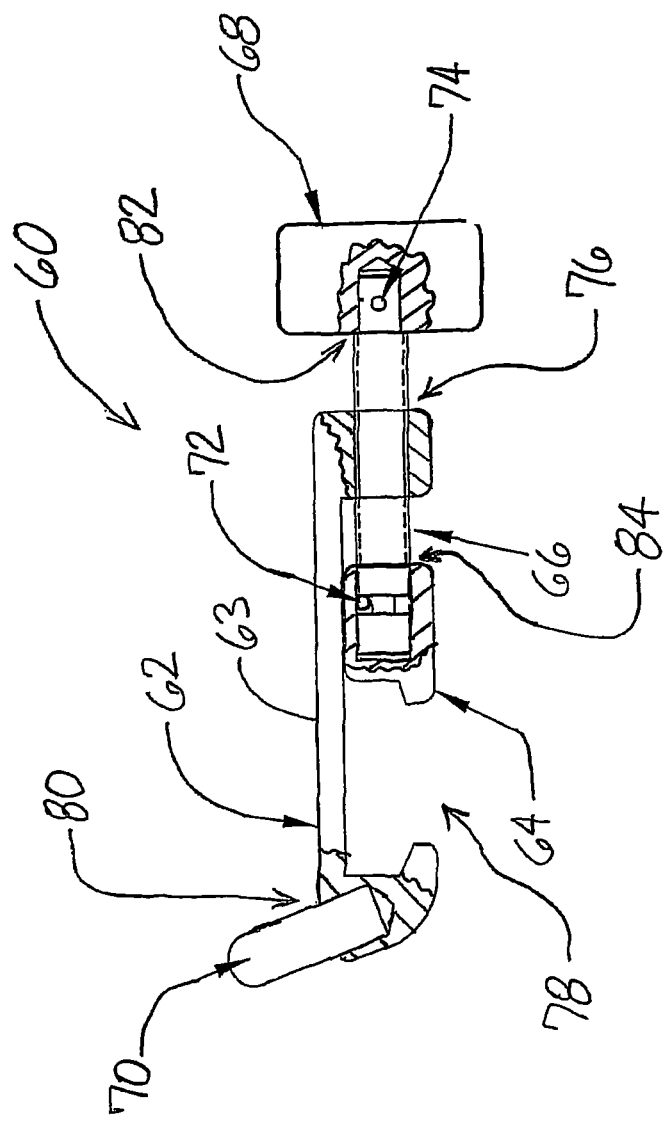
FIG. 2 illustrates a side view of a retractor clamp formed in accordance with an embodiment of the present invention.

FIG. 2 illustrates a side view of the retractor clamp 60 formed in accordance with an embodiment of the present invention. As illustrated in FIGS. 1-2, the retractor clamp 60 includes a main body 62, a base slide 64, a base slide shaft 66, a knob 68, and an L-bar 70. The main body 62 includes a top surface 63. In the illustrated embodiment, the base slide 64 cooperates with at least a portion of the main body 62 to form a gripping assembly. The area between the main body 62 and the base slide 64 forms an opening 78. The opening 78 is adapted to accept the first arm 40, the second arm 50, and/or the cross-bar 30. The elevation of the first arm 40, the second arm 50, or the cross-bar 30 to which the retractor clamp 60 is mounted defines an arm level, as will be referenced below.

The slide shaft 66 and knob 68, as illustrated, are part of a securement assembly to position and maintain the base slide 64 in place. The securement assembly includes an adjustment member for adjusting the securement assembly. In the illustrated embodiment, the adjustment member includes the knob 68. One end of the slide shaft 66 is accepted by an opening 84 in the base slide 64, and held in place by a pin 72. The slide shaft 66 is free to rotate in the opening 84. The opposite end of the slide shaft 66 is accepted by an opening 82 in the knob 68, and secured by a pin 74 so that the slide shaft 66 rotates with the knob 68. The slide shaft 66 also includes a threaded portion that is accepted by a threaded opening 76 in the main body 62. The knob 68 and slide shaft 66 thus may form a thumbscrew for positioning the slide base 64. When the knob 68 is turned, the slide shaft 66 rotates with it. As the slide shaft 66 rotates in the threaded opening 76, the slide shaft also moves forward (or backward) toward the opening 78. The slide base 64 moves forward (or backward) with the slide shaft 66, thereby reducing (or enlarging) the size of the opening 78 to grip (or release) the first arm 40, second arm 50, and/or cross-bar 30. The slide shaft extends horizontally generally at the same elevation as the arm level defined by the first arm 40, second arm 50, and/or cross-bar 30. Further, as shown for the illustrated embodiment, the knob 68 is accessible at substantially the same elevation as the arm level defined by the first arm 40, second arm 50, and/or cross-bar 30.

The L-bar 70 extends from the main body 62. For example, in the illustrated embodiment, the L-bar 70 extends upward from the main body at an angle of about 120 degrees from the top surface 63 of the main body 62 (put another way, at about 120 degrees from the top surface of the first arm 40, second arm 50, or cross-bar 30 which would be accepted by the opening 78 of the retractor clamp 60.)

Figure 3:
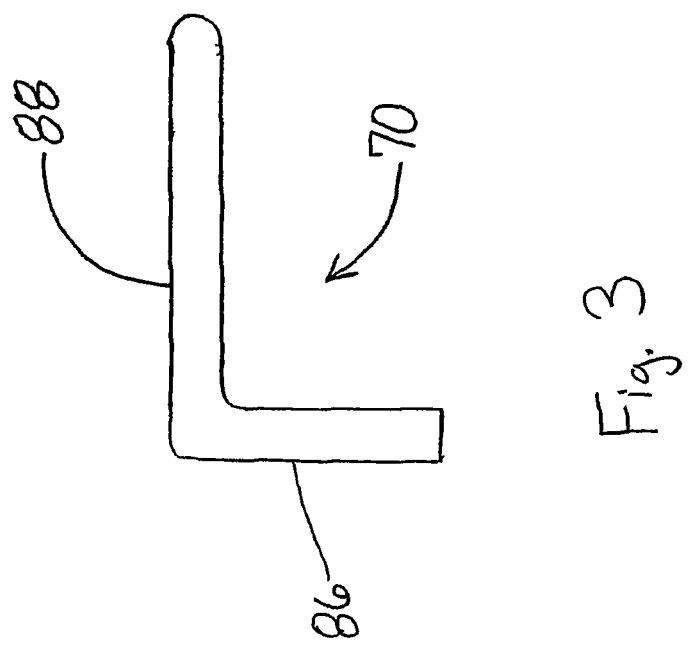
FIG. 3 illustrates a side view of an L-bar formed in accordance with an embodiment of the present invention.

FIG. 3 illustrates a side view of an L-bar 70 formed in accordance with an embodiment of the present invention. The L-bar 70 includes an extension arm 86 and a retractor blade arm 88. In the illustrated embodiment, the extension arm 86 and retractor blade arm 88 share a common end and meet substantially perpendicularly, thereby forming an "L" shape. For example, the extension arm 86 and retractor blade arm may be formed from a single bar of about 0.25" diameter that is bent to form the "L" shape. The L-bar 70 is sized and adapted to provide for placement and adjustability of retractor clamps and blades while maintaining a low profile and reducing obstacles and/or interference to access to the surgical site. The extension arm 86 may be about 0.75" in length, and the retractor blade arm may be about 1" in length. The L-bar 70, in the illustrated embodiment, joins the main body 62 by having the end of the extension arm 86 placed into an L-bar mounting hole 80. The L-bar 70 may, for example, then be welded or soldered in place to the main body 62. With the L-bar 70 attached to the main body 62 and the retractor clamp 60 in place along the first arm 40, second arm 50, or cross-bar 30, the retractor blade arm 88 is located at an elevation slightly higher than the arm level, defining a retractor blade arm level, and extends substantially parallel to the arm to which the retractor clamp 60 is attached in the illustrated embodiment. For example, the retractor blade arm level may be about 0.5 inches higher than the arm level. The retractor blade arm 88 is sized and adapted to accept the blade clamp 90. Alternate embodiments may use differently shaped arms. A T-shape bar, for example, may provide a greater number of potential sites for clamp attachment, but may also increase the profile of the retractor clamp and provide reduced somewhat reduced ease of access.

The blade clamp 90 may be, for example, a universal clamp, of the type known in the art, sized and adapted to provide for adjustability and securability of the retractor blade 100.

Figure 4:
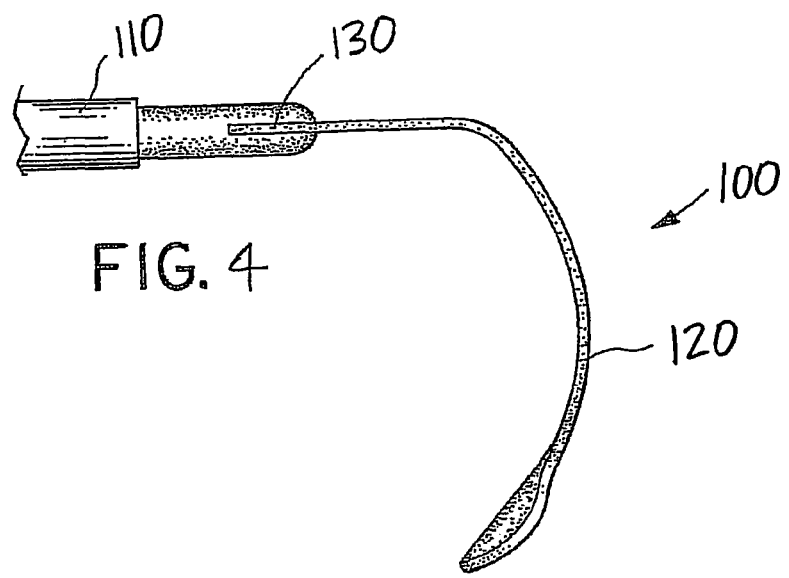
FIG. 4 illustrates a side view of a retractor blade formed in accordance with an embodiment of the present invention.

FIG. 4 illustrates a side view of a retractor blade 100 formed in accordance with an embodiment of the present invention. The retractor blade 100 includes a handle 110 and a blade 120 joined at a junction 130. In FIG. 4 (as well as FIG. 1), the blade 120 is a single sheet formed into a scoop-like shape. In certain embodiments, the blade 120 may be attachable and detachable from the handle 110. The blade 120, for example, may be made of a metal, such as steel or aluminum, of a plastic or polymer, or of any material that is safe to be in contact with human organs and can maintain an appropriately rigid or semi-rigid configuration.

Further, in certain embodiments, a low profile retractor system may include a plurality of retractor blades, including retractor blades having handles of different lengths. For example, the low profile retractor system may include a first retractor blade including a first handle having a first length, and a generally similar second retractor blade including a second handle having a second handle length greater than the first handle length. As an additional example, three or more lengths may be used. For instance, a low profile retractor system may include retractor blades having handle lengths of about 5 inches, about 6.5 inches, and about 8 inches. By providing retractor blades having different handle lengths, a retractor blade may be chosen to provide adequate reach to the tissue desired to be retracted, while also providing for a reduced profile. For example, using a retractor blade having a longer handle than necessary for a given patient or procedure may result in a handle projecting at an inconvenient length, inhibiting access and/or, for example, increasing the risk of a suture becoming entangled with the handle.

Figure 5:
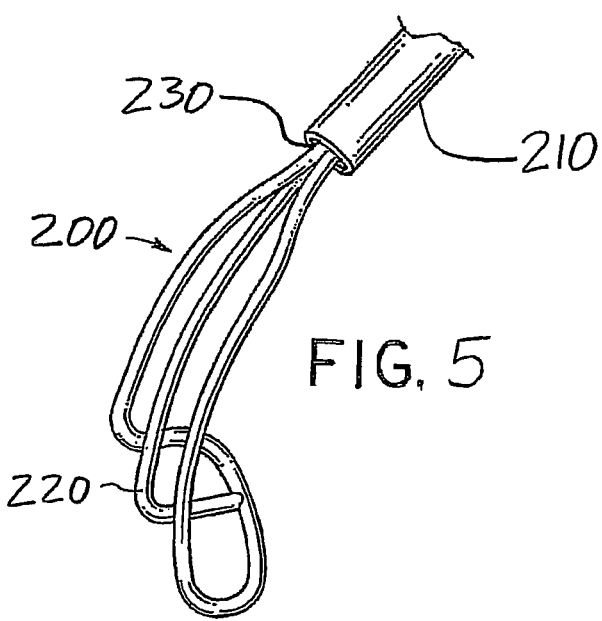
FIG. 5 illustrates a perspective view of a retractor blade formed in accordance with an embodiment of the present invention.

FIG. 5 illustrates a perspective view of a retractor blade 200 formed in accordance with an embodiment of the present invention. The retractor blade 200 includes a handle 210 and a blade 220 joined at a junction 230. The blade 220 includes a wire-like rim 222 outlining a rake-like scoop area.

Additional shapes, sizes, and configurations of blades may vary beyond the embodiments illustrated for use with a variety of sizes, shapes, textures, and/or amounts of tissue to be retracted. For example, where the muscle mass to be retracted is large, but soft, it may be desired to use a blade having a wide contact surface to retract a greater portion of the muscle. Alternatively, it may be desirable to use a narrow blade where only a small mass, and nothing more, is to be retracted. Additionally, various combinations of blade shapes, sizes, and configurations may be used as well. For example, in certain embodiments, a low profile retractor system includes a variety of retractor blades providing a variety of blade profiles and/or handle lengths. Thus, in practice, a surgeon using such a low profile retractor system could select an appropriate retractor based on both the shape of the blade and the length of the handle to provide for the desired retraction, as well as providing improved site access.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A retractor clamp for a low profile retractor system having a plurality of members including first arm, a second arm, and a crossbar defining an arm level, the retractor clamp comprising:
   a main body having at least a first clamping edge;
   a clamp slide having at least a second clamping edge disposed opposite and generally parallel to the first clamping edge;
   an adjustment assembly cooperating with the main body and the clamp slide to adjust the distance between the first clamping edge and second clamping edge, wherein the adjustment assembly, the main body, and the clamp slide form a substantially linear arrangement at arm level that facilitates engagement between the first and second clamping edges and respective opposed sides of a member of the plurality of members to allow movement of the refractor clamp along a length of the member;
   an extension arm permanently affixed to and extending from the main body in a direction outward of the member and at an angle with respect to arm level; and
   a retractor blade arm joined to said extension arm, said retractor blade arm and said extension arm forming a single, integral, L-shaped bar,
   wherein the retractor blade arm and extension arm are configured to place a distal end of the retractor blade arm at a position above arm level, and wherein the retractor blade arm has a principal portion thereof extending in a single direction lengthwise along and parallel to the member, said retractor blade arm sized and adapted to accept a blade clamp for securing a retractor blade thereto.

2. The retractor clamp of claim 1 wherein said extension arm extends from said main body at an obtuse angle.

3. The retractor clamp of claim 1 wherein said main body includes a top surface, and said extension arm extends from said main body at about 120 degrees from said top surface of said main body.

4. The retractor clamp of claim 1 wherein said clamp slide is engaged by a threading member of the adjustment assembly, wherein said clamp slide is movable with respect to the main body by rotation of said knob.

5. The retractor clamp of claim 1 wherein said retractor blade arm level is about 0.5 inches higher than said arm level.

6. A low profile retractor system including:
   a spreader having a plurality of members including first and second arms joined by a cross-bar, said first and second arms being generally parallel, said first and second arms to define an arm level;

a retractor clamp movably and securably joined along a length of at least one of the plurality of members, the retractor clamp including,
　a main body having at least a first clamping edge,
　a clamp slide having at least a second clamping edge disposed opposite and generally parallel to the first clamping edge,
　an adjustment assembly cooperating with the main body and the clamp slide to adjust the distance between the first clamping edge and second clamping edge, wherein the adjustment assembly, the main body, and the clamp slide form a substantially linear arrangement at the arm level that facilitates engagement between the first and second clamping edges and respective opposed sides of a member of the plurality of members to allow movement of the retractor clamp along a length of the member, and
　an extension arm permanently affixed to and extending from the main body in a direction outward of the member and at an angle with respect to arm level,
　a retractor blade arm extending from the extension arm, said retractor blade arm and said extension arm forming a single, integral, L-shaped member, wherein the retractor blade arm and extension arm are configured to place a distal end of the retractor blade arm at a position above arm level, and wherein the retractor blade arm has a principal portion thereof extending in a single direction lengthwise along and parallel to the member;
a retractor blade having a handle and a blade; and
a retractor blade clamp for securing said retractor blade to said retractor blade arm, said retractor blade clamp sized and adapted to accept said retractor blade arm and said handle of said retractor blade.

7. The low profile retractor system of claim 6 wherein said extension arm extends from said main body at an obtuse angle.

8. The low profile retractor system of claim 6 wherein said main body includes a top surface, and said extension arm extends from said main body at about 120 degrees from a top surface of said main body.

9. The low profile retractor system of claim 6 wherein said adjustment assembly includes a threaded member extending substantially at said arm level and substantially perpendicular to said member when said retractor clamp is secured to said member, and wherein said adjustment member includes a knob joined to an end of said threaded member.

10. The low profile retractor system of claim 9 wherein said clamp slide is engaged by said threading member, wherein said clamp slide is actuated by rotation of said knob.

11. The low profile retractor system of claim 6 including a first retractor blade having a first handle and a first blade, and a second refractor blade having a second handle and a second blade, wherein said first handle and said second handle are different lengths.

12. The low profile retractor system of claim 11, wherein said first and second blades are substantially the same size and shape.

13. A retractor clamp for a low profile retractor system having a plurality of members including first arm, a second arm, and a crossbar defining an arm level, the retractor clamp comprising:
　a main body having at least a first clamping edge;
　a clamp slide having at least a second clamping edge disposed opposite and generally parallel to the first clamping edge;
　an adjustment assembly cooperating with the main body and the clamp slide to adjust the distance between the first clamping edge and second clamping edge, wherein the adjustment assembly, the main body, and the clamp slide form a substantially linear arrangement at arm level that facilitates engagement between the first and second clamping edges and respective opposed sides of a member of the plurality of members to allow movement of the refractor clamp along a length of the member;
　an extension arm extending from the main body in a direction outward of the member and at an angle with respect to arm level; and
　a retractor blade arm joined to said main body by said extension arm, wherein the retractor blade arm and extension arm are configured to place a distal end of the retractor blade arm at a position about 0.5 inches higher than said arm level above arm level, and wherein the retractor blade arm has a principal portion thereof extending in a direction lengthwise along the member, said retractor blade arm sized and adapted to accept a blade clamp for securing a retractor blade thereto.

* * * * *